Jan. 24, 1961 J. W. SWEENEY Plant Pat. 2,012

PEAR TREE

Filed March 7, 1960

WITNESS

Addison E. Avery

INVENTOR

James W. Sweeney

Webster & Webster

ATTYS.

United States Patent Office

Plant Pat. 2,012
Patented Jan. 24, 1961

2,012

PEAR TREE

James W. Sweeney, Placerville, Calif.

Filed Mar. 7, 1960, Ser. No. 13,409

1 Claim. (Cl. 47—62)

The present discovery relates to a new and distinct variety of pear tree which bears a white fleshed fruit having an outstanding and highly attractive "Maroon" red exterior or skin color, and which—among other differences—primarily and characteristically distinguishes the variety from the Bartlett (unpatented) and the Max-Red Bartlett (U.S. Plant Patent No. 741), as will later appear in a detailed comparison of the respective varieties.

I discovered the present variety as a bud mutation (bud sport), sometimes referred to as a "limb sport," on a Bartlett pear tree in my orchard located near Placerville, El Dorado County, California; such mutation having come to my attention by reason of observing that it bore fruit having the distinctive "Maroon" red exterior or skin color as compared to the greenish-yellow color of the Bartlett.

Subsequent to my discovery of the variety I asexually reproduced it by grafting buds, from the mutated shoot of the mother-tree, into branches (top-working) of other pear trees in my orchard located as aforesaid.

Additionally, the variety has been asexually reproduced, with my consent, by pomologists of the University of California at Davis, California, by grafting cions of the variety into branches (top-working) of young Old-Home (unpatented) pear trees in the experimental orchard of such university.

The asexual reproductions, in both instances as above, ran true to the original mutation in all respects.

Figure 1:
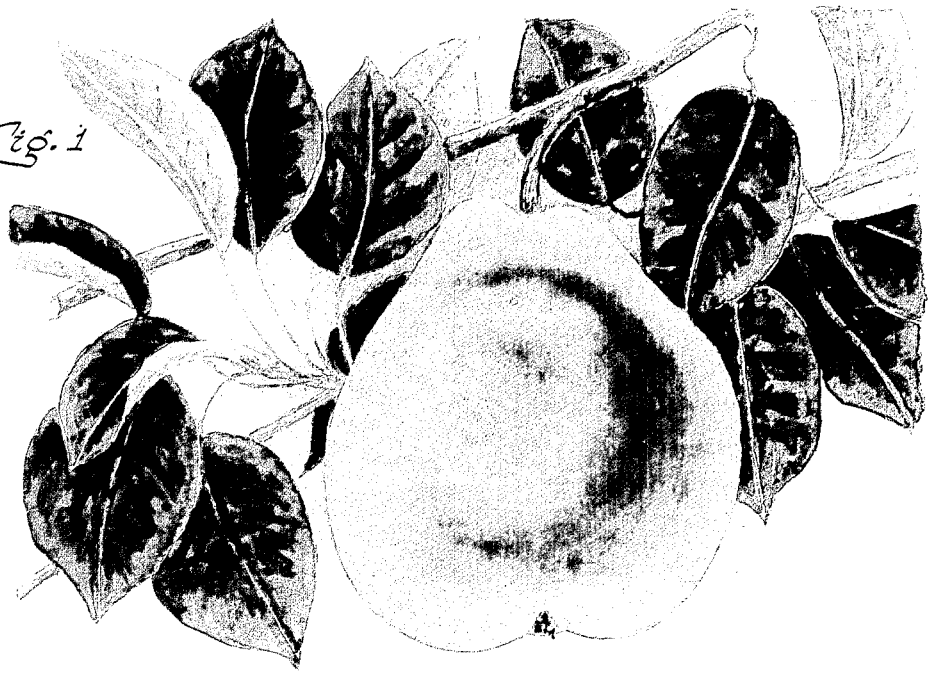
Fig. 1 is an elevation showing one of the fruit, together with twigs and leaves.
Figure 2:
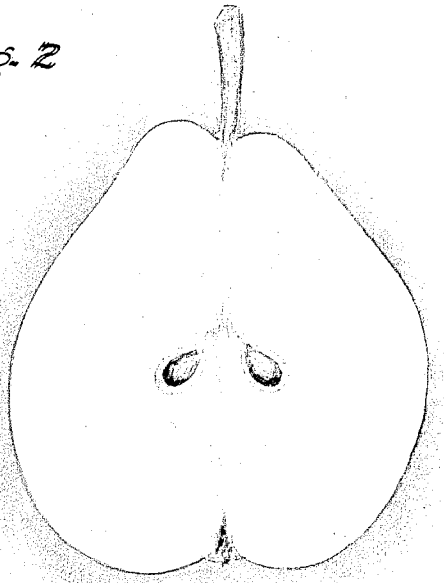
Fig. 2 is a sectional elevation of one of the fruit, with the seeds remaining in place.
Figure 3:
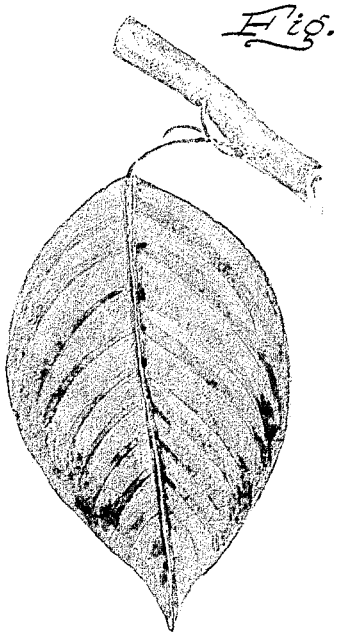
Fig. 3 is an enlarged elevation of one of the leaves, and a portion of the leaf-bearing twig.

Referring to pomological details of this new and distinct variety of pear tree and its fruit, the following is an outline description thereof; all major color plate identifications being by reference to Maerz and Paul Dictionary of Color, except where common terms of color definition are employed.

Tree: Generally similar to the mother-variety, Bartlett.
- *Size.*—Medium.
- *Vigor.*—Vigorous.
- *Form.*—Upright; pyriform.
- *Hardiness.*—Hardy.
- *Production.*—Very productive.
- *Bearing.*—Regular bearer.

Trunk:
- *Size.*—Stocky.
- *Texture.*—Smooth.

Branches: The branches have the same general characteristics as the Bartlett, except that the young shoots (current season's growth, and one-year old wood), have reddish, reddish-brown, or gray-red bark, while similar shoots on the Bartlett have tan or yellowish-brown bark. The bark on the older branches is substantially the same color as that of the Bartlett.
- *Size.*—Stocky.
- *Texture.*—Smooth.

Leaves: Similar to the Bartlett, but apparently slightly darker green.
- *Size.*—Medium. Average length—2⅞". Average width—1½".
- *Form.*—Oval.
- *Apex.*—Taper-pointed.
- *Thickness.*—Medium.
- *Texture.*—Smooth.
- *Margin.*—Finely serrate.
- *Petiole.*—Medium length—average 1¼". Medium thickness.
- *Color.*—Top side—medium green (23–L–3) shading to darker green (23–L–8). Under side—lighter green (21–K–5).

Flower buds: Similar to Bartlett.
- *Size.*—Large.
- *Hardiness.*—Hardy.
- *Form.*—Conic—pointed. Free.
- *Pubescence.*—Slightly pubescent.

Flowers:
- *Blooming period.*—Blooms mid-season with Bartlett.
- *Date of first bloom.*—March 28, 1959.
- *Date of full bloom.*—April 2, 1959.
- *Date of last bloom.*—April 14, 1959.
- *Size.*—Medium.
- *Color.*—White.
- *Pubescence.*—Slightly pubescent.

Fruit:
- *Date of first picking.*—July 28, 1959.
- *Date of last picking.*—August 11, 1959.
- *Size.*—Picking size averaged 2$^{15}/_{16}$" in length and 2$^{9}/_{16}$" at the widest diameter in 1959; such average size being substantially the same as comparable fruit of the Bartlett and Max-Red Bartlett grown under the same conditions of soil and climate.
- *Form.*—Oblong; obtuse; pyriform; tapers toward apex; symmetrical; uniform.
- *Fruit stems.*—Average length—1⅛". Some straight—others curved. Relatively thick.
- *Cavity.*—Small; usually lipped; acute; shallow.
- *Basin.*—Shallow to very shallow; narrow; obtuse; furrowed and wrinkled.
- *Calyx.*—Open or partly open; lobes separated at the base; narrow; acute.

Skin:
- *Thickness.*—Thin.
- *Texture.*—Tender (more tender than either Bartlett or Max-Red Bartlett).
- *Dots.*—Size—small. Number—many. The dots are small and much less conspicuous than those on either Bartlett or Max-Red Bartlett; this feature particularly distinguishing the present variety from said Max-Red Bartlett. Color—russet or gray.
- *Color.*—"Maroon" red (7–L–7) on picking-ripe fruit, becoming slightly lighter. "India" red (7–L–6) on soft-ripe fruit.

Flesh (eating-ripe fruit): Very similar to Bartlett.
- *Juice.*—Juicy.
- *Texture.*—Fine grained; melting; buttery.
- *Flavor.*—Very good; aromatic; delicate; mild.
- *Eating quality.*—Very good.
- *Canning quality.*—Very good.
- *Color.*—White (9–A–1).

Core:
- *Size.*—Medium to large; closed or partly open.
- *Core lines.*—Clasping; distinct.

*Carpellary area.*—Distinct; medium to large. Carpel margins may be tinged with red (not found in Bartlett or Max-Red Bartlett).

*Calyx tube.*—Inclined to be funnel-shaped, with short stem or funnel. Smaller and shorter than Bartlett, but similar.

Seeds:

*Size.*—Medium.

*Width.*—Wide.

*Form.*—Plump; acute.

*Color.*—Tan (7–A–12), shading to brown (56–L–1).

Use: Local; dessert; culinary; shipping.

Keeping quality: Medium.

The tree and its fruit herein described may vary in slight detail due to climatic and soil conditions under which the variety may be grown; the present description of the variety being premised on reproductions grown in the experimental orchard of the University of California at Davis, California.

*Comparative summary*

The over-all, substantially uniform, "Maroon" red exterior or skin color of the fruit of the present variety makes it outstandingly different from the greenish-yellow fruit of the Bartlett. Beyond this, while the present variety retains the Bartlett's general growth and vegetative characteristics, the young shoots have reddish, reddish-brown, or gray-red bark, while shoots on the Bartlett have tan or light brown bark. In maturity, and at the same age, the bark of the branches here has about the same color as the Bartlett.

The present variety resembles the Max-Red Bartlett more than other variety, in that said Max-Red Bartlett is also a bud mutation of the Bartlett and bears fruit having a red exterior or skin color. However, in the present instance, the "Maroon" red exterior or skin color of the fruit definitely sets the variety apart from the Max-Red Bartlett, in that the color here is darker, brighter red and substantially covers the entire surface of the fruit. The two mutations—i.e. the present variety and the Max-Red Bartlett—have been growing and fruiting side by side in the University of California's experimental orchard at Davis, California, and the color distinctions of the fruit have there been clearly and accurately observed.

Further, the Max-Red Bartlett has much less red exterior or skin color at harvest maturity, and is usually striped with alternating areas of dull tannish-red and brownish-red and green; the Max-Red Bartlett fruit being rarely—if ever—a substantially solid red, and there is a sharp contrast in the surface color between picking-ripe and eating-ripe. This is because the greenish portions of the skin of the Max-Red Bartlett turn yellow when eating-ripe. On the other hand, the fruit of the present variety has no such characteristic, and the substantially all-embracing red exterior or skin color—which exists when picking ripe—merely lightens slightly when eating-ripe. This is advantageous for the reason that the fruit is highly attractive at picking maturity, as well as when eating-ripe. The Max-Red Bartlett—on the other hand—as grown under the conditions of the hot interior valleys of California, is usually unattractive at picking maturity because of a dull red color, as well as the aforementioned striped areas of green.

The following is claimed:

A new and distinct variety of pear tree, as illustrated and described, having the general growth and vegetative characteristics of the mother-variety Bartlett, and fruit which in exterior color resembles that of the Max-Red Bartlett more than any other, but in comparison to said Bartlett and Max-Red Bartlett being particularly distinguished by white-fleshed fruit having a substantially over-all "Maroon" red exterior color present in picking-ripe fruit and persisting only lighter red in eating-ripe fruit, by carpel margins tinged with red, and by skin dots which are small and much less conspicuous; and, in further comparison to the Bartlett, by young shoots having reddish, reddish-brown, or gray-red bark.

No references cited.